(12) United States Patent
Legay et al.

(10) Patent No.: US 11,707,309 B2
(45) Date of Patent: Jul. 25, 2023

(54) MODULAR MEDICAL IMPLANT ALLOWING A TARGETED INJECTION

(71) Applicant: INNOPROD MEDICAL, Plaisance-du-Touch (FR)

(72) Inventors: Philippe Alain Lucien Fernand Legay, Yville sur Seine (FR); Frédéric Peyre, Lasserre (FR)

(73) Assignee: INNOPROD MEDICAL, Plaisance-du-Touch (FR)

( * ) Notice: Subject to any disclaimer, the term of this patent is extended or adjusted under 35 U.S.C. 154(b) by 1072 days.

(21) Appl. No.: 16/463,979

(22) PCT Filed: Oct. 12, 2017

(86) PCT No.: PCT/FR2017/000191
§ 371 (c)(1),
(2) Date: May 24, 2019

(87) PCT Pub. No.: WO2018/069583
PCT Pub. Date: Apr. 19, 2018

(65) Prior Publication Data
US 2019/0357956 A1 Nov. 28, 2019

(30) Foreign Application Priority Data

Oct. 13, 2016 (FR) ..................................... 16/01491

(51) Int. Cl.
*A61B 17/86* (2006.01)
*A61B 17/88* (2006.01)
(Continued)

(52) U.S. Cl.
CPC .......... *A61B 17/8685* (2013.01); *A61B 17/72* (2013.01); *A61B 17/84* (2013.01);
(Continued)

(58) Field of Classification Search
CPC ......... A61B 17/72; A61B 17/84; A61B 17/86; A61B 17/864; A61B 17/8685; A61B 17/8802; A61F 2002/4631
See application file for complete search history.

(56) References Cited

U.S. PATENT DOCUMENTS

| | | | | |
|---|---|---|---|---|
| 4,640,271 A | * | 2/1987 | Lower ................ | A61B 17/8685 606/328 |
| 2013/0317503 A1 | * | 11/2013 | Songer ................ | A61B 17/742 606/66 |
| 2015/0157370 A1 | * | 6/2015 | Gross ................ | A61B 17/7241 606/62 |

FOREIGN PATENT DOCUMENTS

| | | | | |
|---|---|---|---|---|
| CN | 104644256 | * | 5/2015 | |
| CN | 104644256 A | * | 5/2015 | ......... A61B 17/8625 |
| WO | 2015/123733 A1 | | 8/2015 | |

OTHER PUBLICATIONS

International Search Report dated Jan. 3, 2018 in corresponding International application No. PCT/FR2017/000191; 4 pages.

(Continued)

*Primary Examiner* — Larry E Waggle, Jr.
(74) *Attorney, Agent, or Firm* — Maier & Maier, PLLC

(57) ABSTRACT

A modular medical implant allowing the targeted injection of a liquid or pasty material into a bone cavity. This implant is produced with four types of modules provided with a lumen and of variable lengths, including: either a male securing principle, referred to as proximal modules, or a female securing principle, referred to as distal modules, or a male securing principle and a female securing principle, referred to as intermediate modules and perforated intermediate modules, that can be secured in a predetermined order and number in order to position the perforated intermediate modules at suitable levels to allow an injection product to be conveyed to and diffused at the targeted locations, via the (Continued)

perforations, while producing the required length of the implant. The implant is intended, in general, for surgical operations and, in particular, for interventional radiology.

9 Claims, 1 Drawing Sheet

(51) Int. Cl.
 *A61B 17/84* (2006.01)
 *A61B 17/72* (2006.01)
(52) U.S. Cl.
 CPC ........ *A61B 17/864* (2013.01); *A61B 17/8802* (2013.01); *A61B 17/8816* (2013.01); *A61B 17/8819* (2013.01)

(56) References Cited

OTHER PUBLICATIONS

Written Opinion of the International Searching Authority dated Jan. 3, 2018 in corresponding International application No. PCT/FR2017/000191; 11 pages.

* cited by examiner

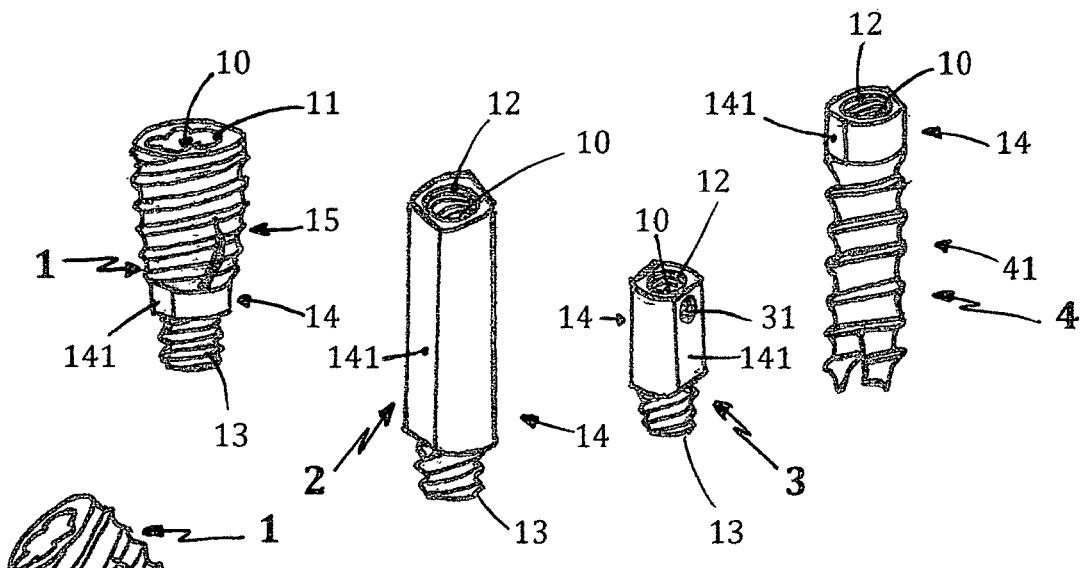
FIG.1
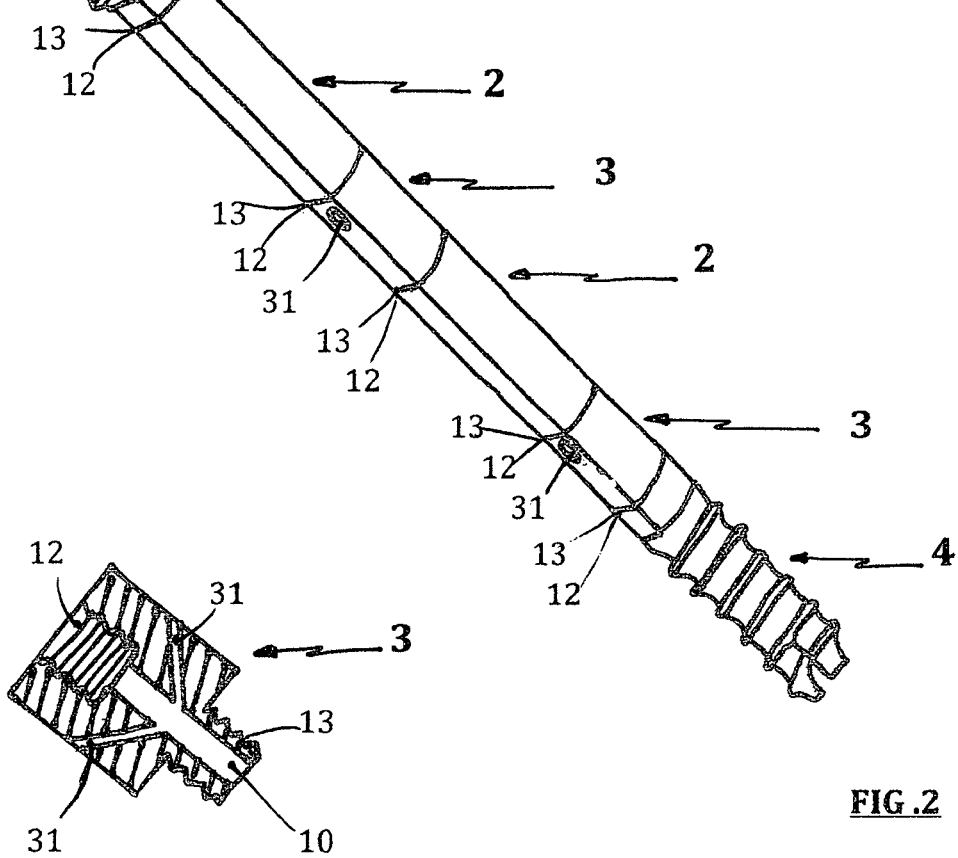
FIG.2
FIG.3

MODULAR MEDICAL IMPLANT ALLOWING A TARGETED INJECTION

FIELD

This invention relates to a modular medical implant that allows for the targeted injection of a liquid or pasty material into a bone cavity, thus favouring filling and/or consolidation, without the risk of constraining any nerve, and/or any other soft portion, that can be present in the vicinity of the injection site.

BACKGROUND

The prior art proposes various materials used in osteosynthesis, nails and screws, cannulated so as to be guided during the installation.

These various materials can be used to convey an acrylic cement, by the intermediary of their lumen, but in no case make it possible to target the injection site or sites.

As the materials that are currently used by practitioners are not dedicated to this technique, either do not make it possible to inject, thus requiring differentiated injections to be made, by practicing other paths first, therefore additional actions that are detrimental for the patient, or do not make it possible to avoid the nerves or the soft portions passing in the cavity, in the vicinity of the implant, giving a risk of pain to the patient.

SUMMARY

This invention aims to give the possibility to the person intervening to resolve these problems, through the use of a modular medical implant that makes it possible, thanks to the combination of various modules, to meet the needs of the practice, and in particular to target the zones, determined beforehand, that are to receive the filling and/or consolidation product.

This purpose is achieved thanks to a set of modules, that can be secured to one another in a predetermined order, so as to position some of said modules provided with lateral perforations at required distances, making it possible to allow the injection product to escape at the targeted locations.

Advantageously, the implant thus formed can form a nail, a pin or a screw of the required length, characterised in that each one of the modules that forms it has a tubular shape of which the section can be circular, provided or not with flat faces over all or a portion of its length, square or polygonal.

Favourably, the flat faces would be intended to cooperate with clamping tools, in that said modules are distributed into distal, intermediate and proximal modules, in that some of the intermediate modules are provided with perforations passing through the inner lumen to the periphery, that can be oriented ascending, descending or perpendicular to said inner lumen, in that said modules can be of different lengths, in such a way as to optimise all of the length possibilities of the final implant and the choice of the positioning of the perforated module or modules, in that each distal module can end with a self-perforating or self-tapping bone thread and comprises a female securing principle intended to cooperate with the male securing principle of one or the other of the intermediate or proximal modules, in that each proximal module starts with a self-perforating and self-tapping bone thread and ends with a male securing principle, intended to cooperate with the female securing principle of one or the other of the intermediate or distal modules, in that each one of the intermediate modules starts with a female securing principle and ends with a male securing principle.

According to the desired embodiment, each male securing principle can be a mechanical thread or one or several peripheral lugs, or any other mechanical means.

Reciprocally, each female securing principle can be a mechanical tapping or one or several peripheral grooves, or any other mechanical means.

Advantageously, each male securing principle of one or the other of the different modules is intended to cooperate indifferently with the female securing principle of one or the other of the other modules, in such a way as to position the perforated modules at suitable levels and obtain the desired length of the modular medical implant.

BRIEF DESCRIPTION OF THE FIGURES

The invention shall be well understood and other characteristics and advantages of the latter shall appear in reference to the accompanying diagrammatical drawings that show, as a non-limiting example, an embodiment of the implant for targeted injection that it relates to.

FIG. 1 shows the four types of modules required for producing a modular medical implant, FIG. 2 shows one of the possible embodiments of a modular medical implant, FIG. 3 shows a cross-section of a perforated intermediate module.

DETAILED DESCRIPTION

FIG. 1 shows the four types of modules required for producing of a modular medical implant, of which:

The proximal module 1 is composed of a male securing principle 13 intended to cooperate with the female securing principle 12 of an intermediate module 2 or of a perforated intermediate module 3 or of a distal module 4, surmounted by a body 14 that can be provided with flat faces 141 intended to receive a clamping tool, then with a bone thread 15 inside of which is machined a female imprint 11 intended to be actuated by a suitable screwdriver.

The intermediate modules 2 are composed of a male securing principle 13 intended to cooperate with a female securing principle 12 of another intermediate module 2 or of a perforated intermediate module 3 or of a distal module 4, surmounted by a body 14 that can be provided with flat faces 141 intended to receive a clamping tool, and with a female securing principle 12 intended to cooperate with a male principle 13 of a proximal module 1 or of an intermediate module 2 or of a perforated intermediate module 3.

Advantageously said intermediate modules 2 can be of different lengths in such a way as to produce the required length of the modular medical implant, while still positioning the perforated intermediate module or modules 3 at suitable levels in order to allow the injection product to escape at the targeted locations.

The perforated intermediate modules 3 are composed according to the same principle as the intermediate modules 2 and are provided with perforations 31 passing through the inner lumen 10 to the periphery of the body 14.

Usefully, said perforations 31 can be orientated perpendicularly to the inner lumen 10, ascending opening towards the female securing principle 12 or descending opening towards the male securing principle 13.

The distal module 4 is composed of a bone thread 41 surmounted by a body 14 that can be provided with flat faces 141 intended to receive a clamping tool, and with a female securing principle 12 intended to cooperate with a male securing principle 13 of an intermediate module 2 or of a perforated intermediate module 3 or of a proximal module 1.

Usefully, all of the modules are passed through longitudinally by lumens 10 of the same diameter that provide a continuity from the proximal module to the distal module, during the composition of the modular implant, allowing for the conveying of a liquid or pasty material from the female imprint 11 to the perforations 31.

FIG. 2 shows one of the possible embodiments of a modular medical implant composed, by way of example, of a proximal module 1 of which the male securing principle 13 cooperates with the female securing principle 12 of an intermediate module 2 of which the male securing principle 13 cooperates with the female securing principle 12 of a perforated intermediate module 3 of which the male securing principle 13 cooperates with the female securing principle 12 of an intermediate module 2 of which the male securing principle 13 cooperates with the female securing principle 12 of a perforated intermediate module 3 of which the male securing principle 13 cooperates with the female securing principle 12 of a distal module 4.

Advantageously, the intermediate modules 2 can be of different lengths in such a way as to produce the required length of the modular medical implant, while still positioning the perforated intermediate module or modules 3 at suitable levels in order to allow the injection product to escape at the targeted locations.

FIG. 3 shows a cross-section view of a perforated intermediate module 3 of which the perforations 31 can be oriented perpendicularly to the inner lumen 10 or slanted, ascending from the lumen 10 to the female securing principle 12 or descending from the lumen 10 to the male securing principle 13.

As appears in all of the above, the invention provides a modular medical implant, in particular for osteosynthesis, allowing a targeted injection and having, in relation to the approved materials of the prior art or borrowed from other disciplines, the determinant advantage of making it possible to target the injection site or sites of a liquid or pasty material into a bone cavity, in particular in order to carry out a filling and/or a consolidation in the best conditions, by preventing any risk of constraining any nerve and/or any other soft portion that may be present in the vicinity of the injection site.

It goes without saying that the invention is not limited to the embodiment described here as an example, but that it extends to all of the equipment and all of the embodiments covered by the accompanying claims hereinafter.

The invention claimed is:

1. A modular medical implant allowing a targeted injection into a targeted injection site, the modular medical implant comprising a proximal module at one end, a distal module at another end, and one or several intermediate modules positioned between the proximal module and the distal module, wherein:

the proximal module comprises:
  a first proximal module end,
  a second proximal module end,
  a proximal module length extending from the first proximal module end to the second proximal module end,
  a proximal module body configured to receive a clamping tool between the first proximal module end and the second proximal module end,
  a female imprint at the first proximal module end from which extends an inner lumen passing longitudinally through the proximal module length to the second proximal module end,
  an exterior bone thread forming the first proximal module end extending along the proximal module length to the proximal module body, and
  a male securing principle extending from the second proximal module end along the proximal module length to the proximal module body;

the one or several intermediate modules, of which one or several are perforated intermediate modules provided with perforations, each of the one or several intermediate modules comprises:
  a first intermediate module end,
  a second intermediate module end,
  an intermediate module length extending from the first intermediate module end to the second intermediate module end,
  an intermediate module body configured to receive a clamping tool extending from the first intermediate module end and towards the second intermediate module end
  a female securing principle at the first intermediate module end from which extends an inner lumen passing longitudinally through the intermediate module length to the second intermediate module end, the perforations of the one or several perforated intermediate modules pass through from the lumen to a periphery of the intermediate module body, allowing for conveying of a liquid or pasty material to targeted locations, and
  a male securing principle extending from the second intermediate module end to the intermediate module body; and the distal module comprises:
  a first distal module end,
  a second distal module end,
  a distal module length extending from the first distal module end to the second distal module end,
  a distal module body configured to receive a clamping tool extending from the first distal module end and towards the second distal module end,
  a female securing principle at the first distal module end from which extends an inner lumen passing longitudinally through the distal module length to the second distal module end,
  an exterior bone thread extending from the distal module body along the distal module length to form the second distal module end, wherein all of the modules required for producing a desired length of the modular medical implant, are secured to one another by an intermediary of cooperating sets comprising the male securing principles and the female securing principles, thus making it possible to position the perforations of the perforated intermediate module or modules at required levels to target injection of a liquid or pasty material, and wherein the modular medical implant is configured to target a targeted injection site localized inside a bone cavity in order to carry out a filling and/or a consolidation of said cavity, while preventing any risk of constriction in the vicinity of the injection site.

2. The modular medical implant allowing a targeted injection according to claim 1, wherein each of the modules is of a different lengths, in such a way as to optimise all length possibilities of a final implant and a choice of the positioning of the perforated intermediate module or modules.

3. The modular medical implant allowing a targeted injection according to claim 1, wherein each one of the modules is a tube defining the inner lumens providing the modular medical implant with a body whose section is circular, square or polygonal.

4. The modular medical implant allowing a targeted injection according to claim 3, wherein the section of the body is circular and each of the modules are provided with flat faces to be able to cooperate with the clamping tool.

5. The modular medical implant allowing a targeted injection according to claim 1, wherein the perforations of the perforated intermediate module or modules are oriented perpendicularly to the inner lumen, or slanted by ascending and opening towards the female securing principle or by descending and opening towards the male securing principle.

6. The modular medical implant allowing a targeted injection according to claim 1, wherein each male securing principle is intended to cooperate with each female securing principle.

7. The modular medical implant allowing a targeted injection according to claim 1, wherein each male securing principle is a mechanical thread, or one or several peripheral lugs, or any other mechanical means.

8. The modular medical implant allowing a targeted injection according to claim 1, wherein each female securing principle is a mechanical tapping, or one or several peripheral grooves, or any other mechanical means.

9. The modular medical implant allowing a targeted injection according to claim 1, wherein the exterior bone thread of the proximal module and the exterior bone thread of the distal module are provided with self-perforating and self-tapping bone threads.

\* \* \* \* \*